US010288548B2

(12) United States Patent
Silva et al.

(10) Patent No.: US 10,288,548 B2
(45) Date of Patent: May 14, 2019

(54) WAVELET-BASED ANALYSIS FOR FOULING DIAGNOSIS OF AN AIRCRAFT HEAT EXCHANGER

(71) Applicant: Hamilton Sundstrand Corporation, Windsor Locks, CT (US)

(72) Inventors: Andre A. Silva, Manchester, CT (US); Nayeff A. Najjar, Willington, CT (US); Shalabh Gupta, Manchester, CT (US); Paul M. D'Orlando, Simsbury, CT (US); Rhonda Dawn Walthall, Escondido, CA (US)

(73) Assignee: HAMILTON SUNDSTRAND CORPORATION, Windsor Locks, CT (US)

( * ) Notice: Subject to any disclaimer, the term of this patent is extended or adjusted under 35 U.S.C. 154(b) by 413 days.

(21) Appl. No.: 14/689,467

(22) Filed: Apr. 17, 2015

(65) Prior Publication Data

US 2016/0305865 A1 Oct. 20, 2016

(51) Int. Cl.
*G01N 17/00* (2006.01)
*G01M 15/04* (2006.01)
*F28F 27/00* (2006.01)
*G01N 25/18* (2006.01)

(52) U.S. Cl.
CPC ........... *G01N 17/008* (2013.01); *F28F 27/00* (2013.01); *G01N 25/18* (2013.01)

(58) Field of Classification Search
CPC ............... G01N 17/008; F28F 27/00

USPC ........................................................ 702/183
See application file for complete search history.

(56) References Cited

U.S. PATENT DOCUMENTS

| | | | | |
|---|---|---|---|---|
| 6,907,383 | B2 * | 6/2005 | Eryurek | G01F 1/363 |
| | | | | 702/100 |
| 7,290,450 | B2 * | 11/2007 | Brown | G01F 1/666 |
| | | | | 73/579 |
| 7,455,099 | B2 | 11/2008 | Osborn et al. | |
| 7,827,006 | B2 | 11/2010 | Miller | |
| 7,940,189 | B2 * | 5/2011 | Brown | F16K 37/0075 |
| | | | | 340/605 |
| 7,949,495 | B2 * | 5/2011 | Wiklund | G01F 1/363 |
| | | | | 702/183 |
| 8,064,722 | B1 * | 11/2011 | Rose-Pehrsson | G06K 9/527 |
| | | | | 327/1 |
| 2001/0022509 | A1 * | 9/2001 | Schulmayr | H02J 7/0073 |
| | | | | 320/132 |
| 2003/0173072 | A1 * | 9/2003 | Vinegar | B09C 1/02 |
| | | | | 166/66.5 |

(Continued)

*Primary Examiner* — Ly D Pham
(74) *Attorney, Agent, or Firm* — Cantor Colburn LLP

(57) ABSTRACT

A method and apparatus for estimating a fouling state of a heat exchanger of an aircraft. Training sensor measurements are obtained of a parameter related to operation of the heat exchanger and a wavelet transform is applied to the training sensor measurements to obtain wavelet data. Data reduction is performed on the wavelet data to obtain representative features indicative of the training sensor measurements. A classifier is then trained to assign suitable fouling classes to the representative features. The trained classifier is used on testing sensor measurements from the heat exchanger to assign a fouling class to the testing sensor measurements in order to estimate the fouling state of the heat exchanger.

15 Claims, 6 Drawing Sheets

(56) References Cited

U.S. PATENT DOCUMENTS

| | | | |
|---|---|---|---|
| 2005/0128125 A1* | 6/2005 | Li | F41H 11/12 342/22 |
| 2005/0177317 A1* | 8/2005 | Hsiung | G01N 33/0031 702/22 |
| 2006/0014296 A1* | 1/2006 | Brons | G01N 17/008 436/171 |
| 2006/0025897 A1* | 2/2006 | Shostak | B60C 23/005 701/1 |
| 2006/0116555 A1* | 6/2006 | Pavlidis | A61B 5/01 600/300 |
| 2007/0244271 A1* | 10/2007 | Muhle | C08F 2/00 526/60 |
| 2013/0013145 A1* | 1/2013 | Ernst | B64D 13/06 701/36 |
| 2013/0048535 A1* | 2/2013 | Wang | C10G 7/10 208/47 |
| 2014/0008035 A1 | 1/2014 | Patankar et al. | |
| 2014/0244051 A1* | 8/2014 | Rollins | F04D 27/004 700/282 |
| 2015/0217153 A1* | 8/2015 | Jones | A62C 3/08 169/62 |
| 2015/0254555 A1* | 9/2015 | Williams, Jr. | G06N 3/0454 706/14 |
| 2015/0272106 A1* | 10/2015 | Schertz | A01M 7/0089 239/11 |

\* cited by examiner

WAVELET-BASED ANALYSIS FOR FOULING DIAGNOSIS OF AN AIRCRAFT HEAT EXCHANGER

BACKGROUND OF THE INVENTION

The present invention is related to aircraft Environmental Control Systems (ECSs) and in particular to a system and method for estimating a fouling condition of a heat exchanger of an ECS The Environmental Control System (ECS) of an aircraft has two basic functions: i) to provide a fresh cabin air supply, and ii) to deliver thermal control and air pressure to an aircraft cabin in order to provide comfort to crew members and passengers. One component of the ECS is a heat exchanger, which maintains the above two functions by proper cooling of engine bleed air. Aircraft heat exchangers can suffer from performance degradation due to a phenomenon called fouling that occurs when there is unwanted accumulation of external substances, debris, and/or organisms that contaminate the surface of heat exchanger fins. Fouling degrades the performance of the heat exchanger by reducing thermal efficiency, introducing a decrease of heat flux, and adding stress on the cooling mechanism of the heat exchanger. Due to the frequency at which fouling occurs, the heat exchanger is generally scheduled for periodic maintenance, thus incurring economic losses and unwanted interruption of the aircraft operation. Therefore, there is a need to develop a real-time diagnostic tool for detecting and diagnosing fouling of the heat exchanger in-situ.

Since fouling occurs in complex environments where parameters such as altitude levels, ambient temperatures and passenger loads are varying, diagnosing fouling conditions during a maintenance operation on the ground can be difficult.

BRIEF DESCRIPTION OF THE INVENTION

In one aspect, a method of estimating a fouling state of a heat exchanger of an aircraft includes: obtaining training sensor measurements of a parameter related to operation of the heat exchanger; applying a wavelet transform to the training sensor measurements to obtain wavelet data; performing data reduction on the wavelet data to obtain representative features indicative of the training sensor measurements; training a classifier to assign suitable fouling classes to the representative features; and applying the trained classifier to testing sensor measurements from the heat exchanger to assign a fouling class to the testing sensor measurements in order to estimate the fouling state of the heat exchanger.

In another aspect, an apparatus for estimating a fouling state of a heat exchanger of an aircraft, includes: a model of the heat exchanger; one or more sensors configured to obtain training sensor measurements of a parameter related to an operation of the model of the heat exchanger; and a processor configured to: apply a wavelet transform to the training sensor measurements to obtain wavelet data; perform data reduction on the wavelet data to obtain representative features, train a classifier to assign suitable fouling classes to the representative features, and apply the trained classifier to testing sensor measurements from the heat exchanger to assign a fouling class to the testing sensor measurements in order to estimate the fouling state of the heat exchanger.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION OF THE INVENTION

The present invention estimates a level of fouling of an Environmental Control System (ECS) of an aircraft using wavelet analysis and a method of data reduction on simulated or training data from the ECS. The method disclosed herein uses a classifier that is trained using the features obtained from wavelet analysis of the time-domain measurements, and data reduction of this wavelet transformed data. The classifier is then capable of learning a behavior of a model of a heat exchanger of the ECS under different fouling conditions, including nominal conditions in which there is no fouling. The trained classifier can then be used on real-time data from the ECS to determine the level of fouling of the ECS. Therefore, the methods disclosed herein may be used to operate the ECS as well as to monitor and/or regulate operation of the ECS.

Figure 1:
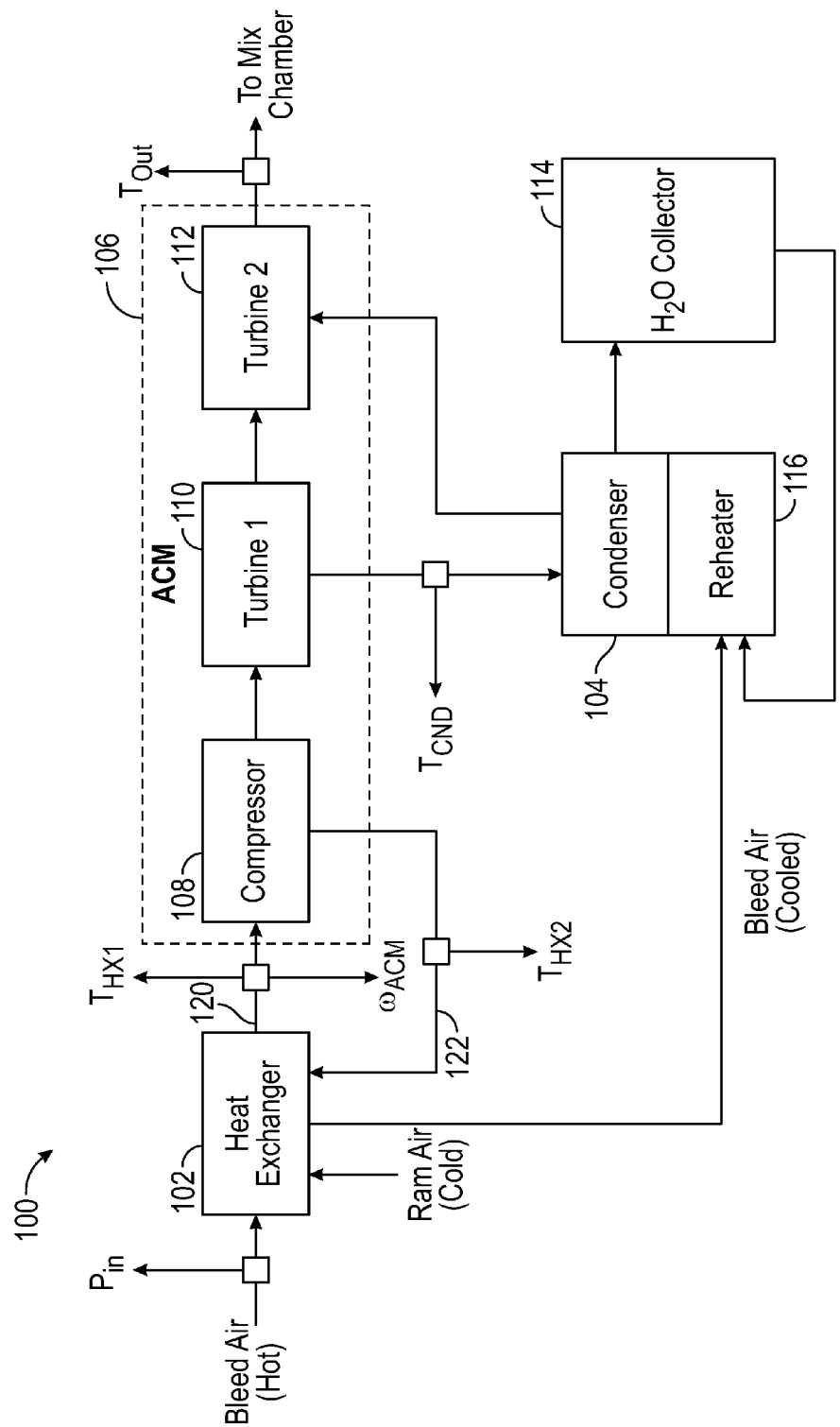
FIG. 1 shows an exemplary Environmental Control System (ECS) of an aircraft that can be diagnosed using the methods disclosed herein.

FIG. 1 shows an exemplary Environmental Control System (ECS) 100 of an aircraft that can be diagnosed using the methods disclosed herein. The ECS 100 delivers pressurized and thermally controlled air to a flight cabin of an aircraft. The ECS 100 includes a heat exchanger 102, condenser (CND) 104 and an Air Cycle Machine (ACM) 106.

The heat exchanger 102 receives bleed air from an aircraft engine as well as ram air. In one embodiment, the heat exchanger 102 is a plate-fin heat exchanger which is constructed of a set of parallel aluminum plates stacked upon each other. The spaces between these plates are composed of square-finned chambers used to transfer heat between the bleed air (hot) and the ram air (cold). Heated ram air is then circulated through a first fluid line 120 between the heat exchanger 102 and the ACM 106 in order to operate the ACM 106. Spent fluid from the ACM 106 is returned to the heat exchanger 102 through a second fluid line 122.

The ACM 106 is an in-house refrigerant unit for the aircraft and uses ram air as a medium for cooling conditioned bleed air that is ultimately used for cabin cooling. The ACM 106 includes a compressor 108, a first turbine 110 and a second turbine 112. The compressor 108 is used to compress the ram air to increase its temperature and pressure. The first turbine 110 and second turbine 112 utilize the thermal energy of the compressed ram air to spin a shaft on which the compressor 108 and first and second turbines 110 and 112 are located.

The condenser 104 facilitates heat transfer by being a catalyst for converting vapor into a liquid. The first turbine 110 may provide a gas or steam to the condenser 104 for condensing. The condensed heat may be stored at a collecting unit 114 from which it may be circulated to a reheater 116 in thermal communication with the condenser 104. The reheated steam may then be used at the second turbine 112.

The heat exchanger 102, compressor 108 and two turbines 110 and 112 degrade in various ways. The heat exchanger 102 is subject to fouling due to surface contamination. Fouling occurs due to growth of living organisms on the surface of the heat exchanger 102 or by deposition of non-living substances, which can be organic or inorganic. The effects of fouling include contamination of the heat exchanger surfaces, which thereby reduces the flow of ram air through the plate fins, thus reducing an amount of heat transfer. This degradation affects the thermal efficiency of the heat exchanger 102 and the heat flux across the heat exchanger 102.

Sensors are coupled to the ECS 100 at various locations to measure various parameters related to the ECS 100 and/or the heat exchanger 102. Pressure sensor $P_{in}$ measures an input pressure of the bleed air to the heat exchanger 102. Temperature sensor $TH_{X1}$ measures a primary heat exchanger output temperature, i.e., the temperature of gas circulating from the heat exchanger 102 to the compressor 108. Temperature sensor $TH_{X2}$ measures a secondary heat exchanger temperature, i.e., the temperature of spent gas circulating from the compressor 108 to the heat exchanger 102. Temperature sensor $T_{CND}$ measures a condenser inlet temperature. Temperature sensor $T_{OUT}$ measures a temperature at an output of the ACM 106. Angular speed sensor $\omega_{ACM}$ measures an angular speed of the ACM 106, i.e., the shaft of the ACM 106.

Figure 2:
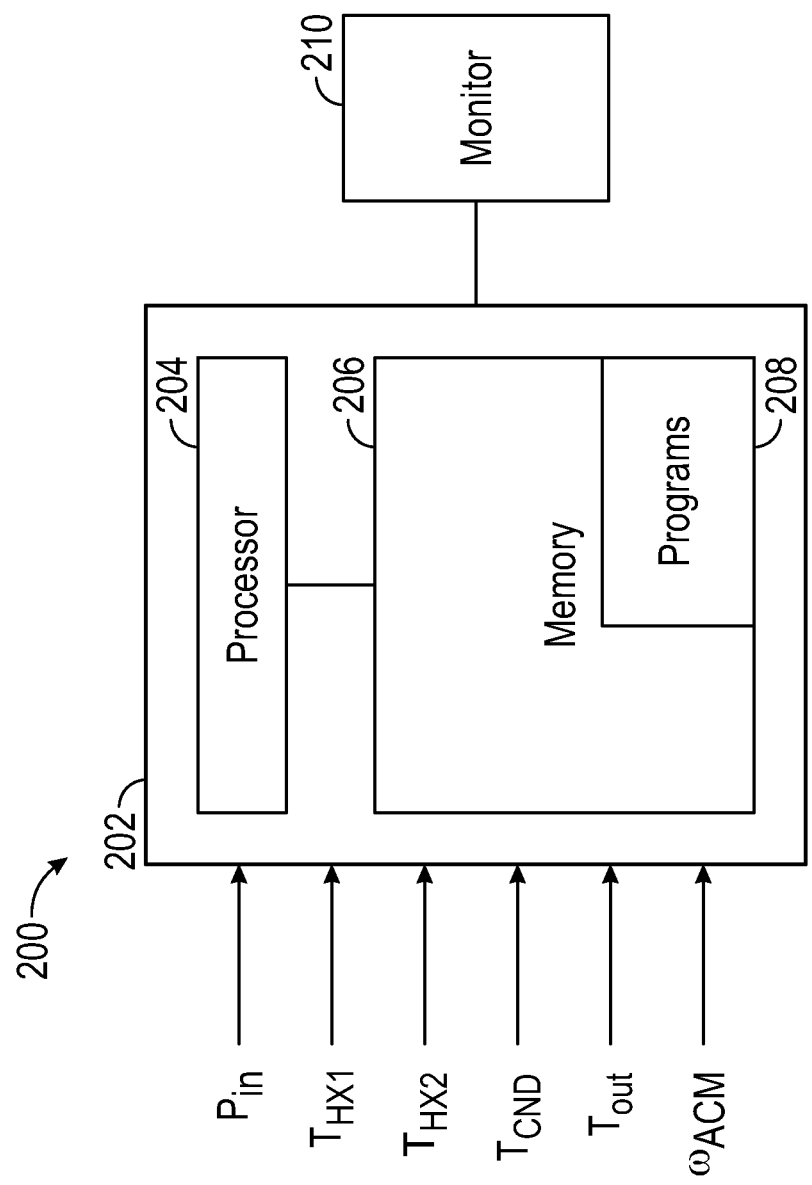
FIG. 2 shows a system suitable for estimating the fouling condition of the ECS using the measurements obtained from the sensors of FIG. 1.

FIG. 2 shows a system 200 suitable for estimating the fouling condition of the ECS 100 using the measurements obtained from the sensors in FIG. 1. The system 200 includes a control unit 202 including a processor 204 and a memory storage device 206. The memory storage device 206 may include a non-transitory computer-readable medium such as a solid-state memory device. The memory storage device 206 may have programs or instructions 208 stored therein which when read by the processor 204 enable the processor 204 to estimate the fouling condition of the ECS 100. The processor 204 receives the measurements taken from the sensors of FIG. 1 and outputs a diagnosis of a fouling condition of the ECS 100 to a monitor 210 for display. The diagnosis may be seen, for example, by the pilot of the aircraft, allowing the pilot to schedule a maintenance procedure or to take appropriate in-flight actions. The method of the present invention for estimating the fouling condition is discussed further below.

Figure 3A:
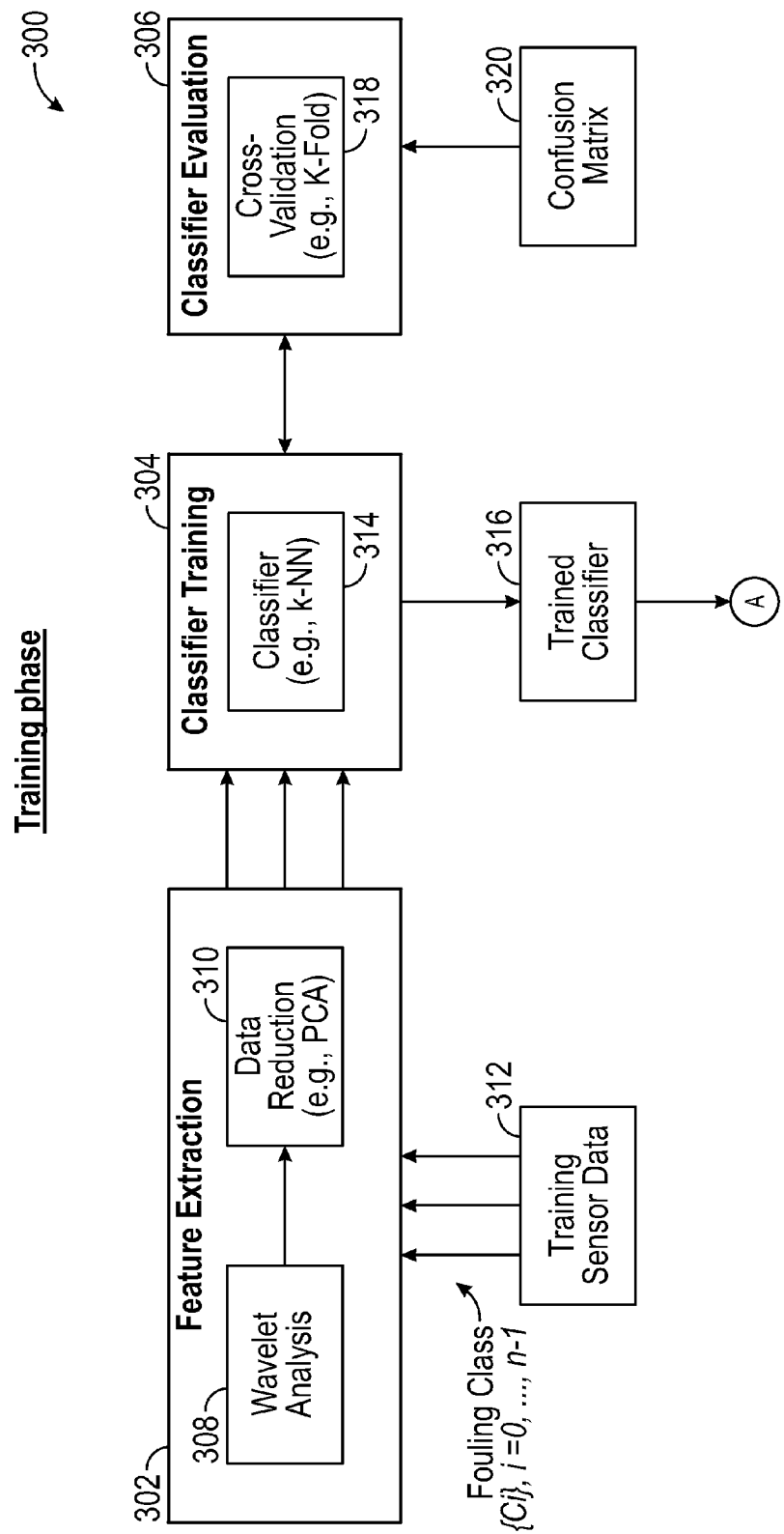
FIGS. 3A and 3B show a schematic diagram of an illustrative method for estimating a fouling condition of the ECS in one embodiment of the present invention.
Figure 3B:
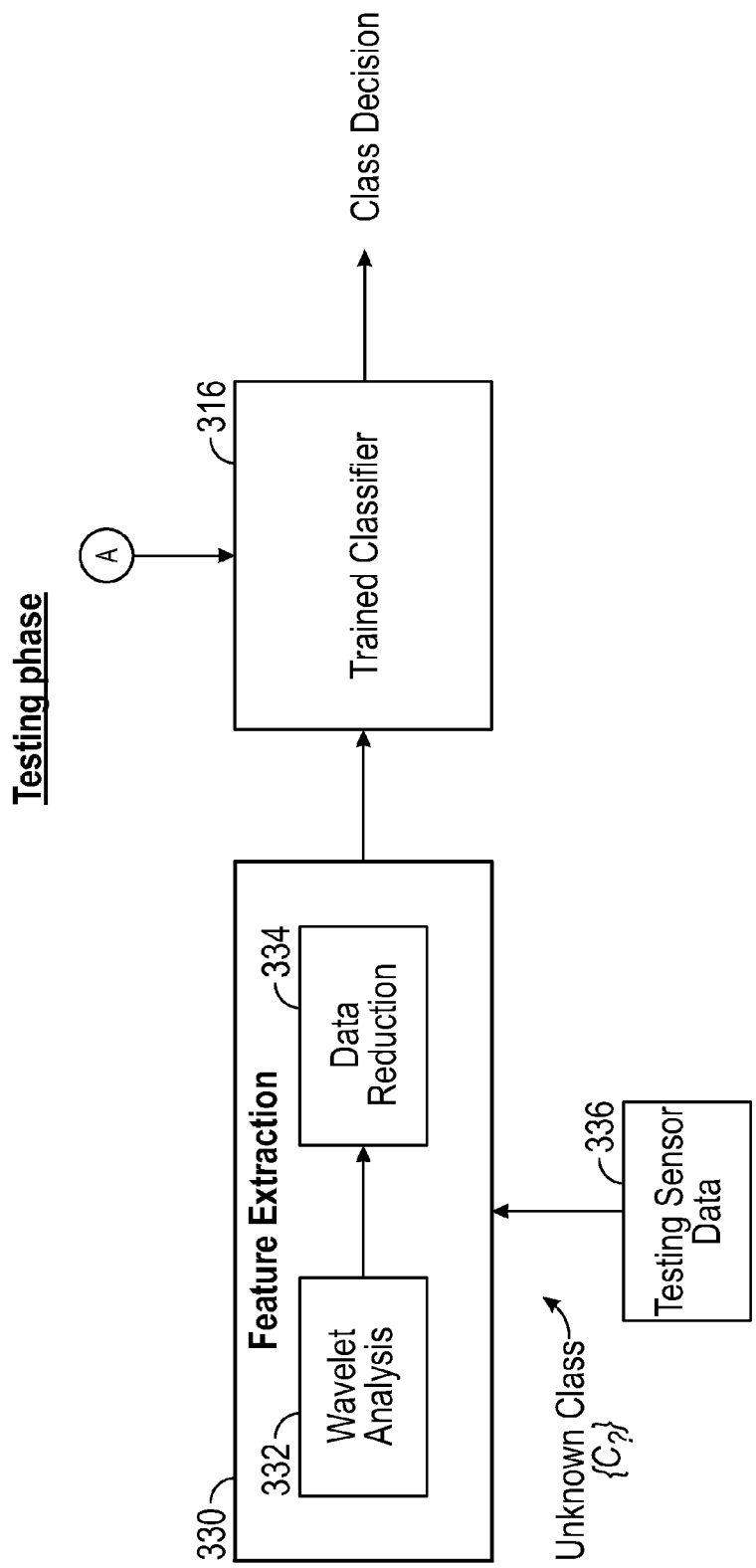

FIGS. 3A and 3B show a schematic diagram 300 of an illustrative method for estimating a fouling condition of the heat exchanger 102 of the ECS 100 in one embodiment of the present invention. The method includes a training phase (shown in FIG. 3A) and a testing phase (shown in FIG. 3B). The training phase uses a set of training sensor data which can be simulated sensor data produced from a model of the heat exchanger 102 or data from operation of a heat exchanger 102 in a laboratory or controlled setting. The training phase results in a trained classifier 316 which is then used in the testing phase with real-time sensor data obtained from a heat exchanger 102. The training phase and the testing phase may be performed or executed using the processor 204 of FIG. 2.

The training phase includes a feature extraction process 302, a classifier training process 304 and a classifier evaluation process 306. The feature extraction process ("feature extractor") 302 receives training sensor data 312. The feature extraction process 302 includes a wavelet analysis process ("wavelet analyzer") 308 and a data reduction process ("data reducer") 310. In one embodiment, the data reduction process 310 uses Principal Component Analysis (PCA). The wavelet analysis process 302 performs a wavelet transform of the training data 312 to obtain corresponding wavelet data in a wavelet domain. The wavelet data includes temporal and spectral information of the sensor measurements. The wavelet data from the wavelet analysis process 302 is input into the data reduction process 310. Principal Component Analysis may be applied (at data reduction process 310) on the wavelet data to reduce the dimensionality of the data, thereby enabling the extraction of useful features in terms of principal components of the data. While Principal Component Analysis (PCA) is disclosed herein in an exemplary embodiment, any form of data reduction may be used. Such data reduction methods generally transform the data to obtain one or more representative features of the wavelet data in a lower dimensional space. The feature extraction process 302 sends the representative features to the classifier training process 304.

The classifier training process 304 uses the representative features to classify the fouling condition of the heat exchanger 102. In an illustrative embodiment, the fouling condition may belong to one of three classes. A first class (e.g., the nominal class) includes fouling levels from 0% to 25% corresponding to minimal or non-existent fouling. A second class (e.g., the cautionary class) includes fouling levels from 25% to 50% corresponding to an amount of fouling that requires service at the next available opportunity. A third class (e.g., the critical class) includes fouling levels from 50% to 100% corresponding to an amount of fouling that requires immediate service. Although three fouling classes are discussed in the above illustration, any number of fouling classes can be defined in alternate embodiments. The fouling classes of the heat exchanger 102 may be known or defined a priori.

The classifier training process 304 creates a trained classifier 316 that is suitable for use in-situ during the testing phase. The trained classifier 316 is trained using a model of the ECS 100 operating under various fouling conditions of the heat exchanger 102, such as a "nominal fouling" condition and various predefined levels of fouling. The trained classifier 316 is trained while taking into account uncertainties present in the data. Such uncertainties may include process or measurement noise and un-modeled physical dynamics. To train the trained classifier 316, the wavelet analysis process 308 first transforms time-domain sensor data obtained from a model of the ECS to the wavelet domain. Noise reduction and the enhancement of patterns generated under different fouling conditions can be performed in the wavelet domain. Subsequently, representative features (e.g. principal components) are extracted from the wavelet domain using the data reduction process 310. These features can be classified into different fouling classes, which are then used by the classifier training process 304 to train the classifier 314 to obtain the trained classifier 316. In one embodiment, the classifier 314 uses a k-Nearest Neighbor (k-NN) algorithm as a decision function for classifying the fouling severity of the heat exchanger given a set of training sensor measurements. The trained classifier 316 can then be implemented for real-time fouling diagnosis of the heat exchanger 102.

Figure 4:
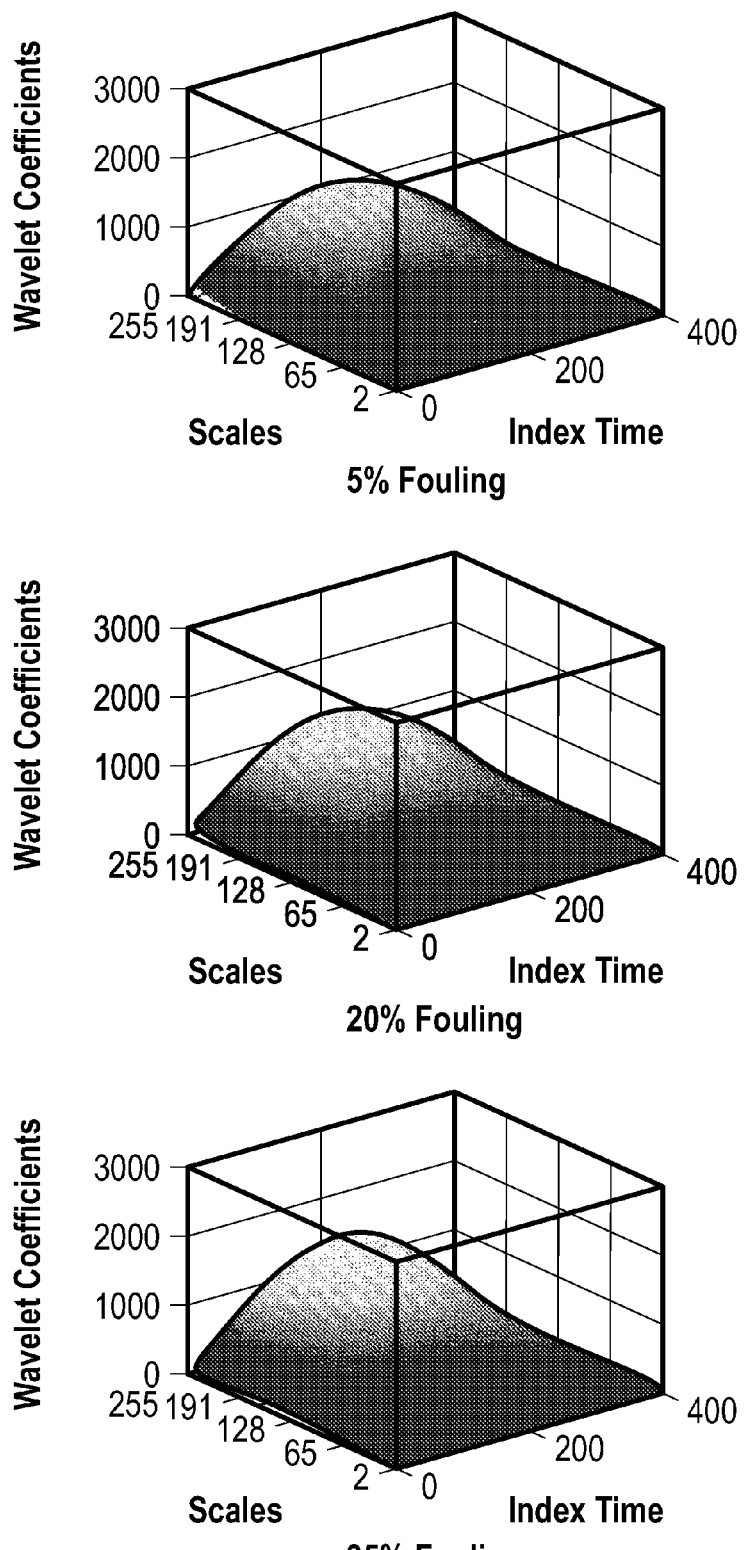
FIG. 4 shows various wavelet surface plots in a wavelet domain of sensor data for a heat exchanger model.
Figure 4:
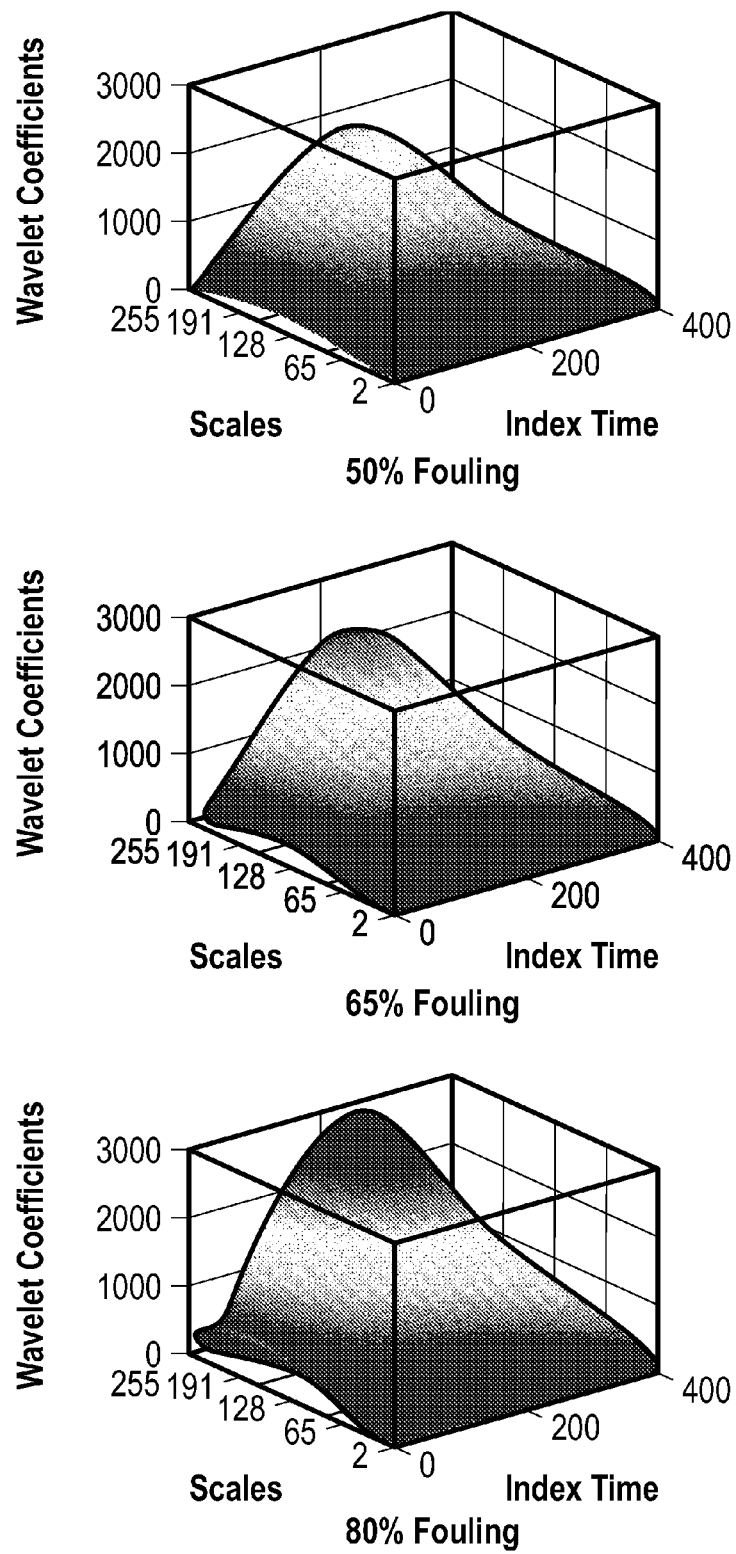

FIG. 4 shows various wavelet surface plots in a wavelet domain for a heat exchanger model. The wavelet surface plots are shown in increasing order of fouling severity. The trained classifier 316 utilizes the features from the wavelet surfaces obtained from the measurements in the heat exchanger model to determine the degree of fouling associated with the measurements.

The Classifier Evaluation process 306 can be used to evaluate a performance of the classifier 314. In one embodiment, the performance of the classifier 314 may be evaluated using a K-fold Cross-Validation (CV) algorithm 318. For each iteration, the sensor data are partitioned into random groups, where a portion of the groups is used for training the classifier 314 and the remaining groups are used for testing the classifier 314. Multiple iterations of the K-fold CV algorithm 318 may be tabulated into a confusion matrix 320 which summarizes the classifier's performance in correctly assigning one or more classes to the representative features related to the training sensor measurements. The confusion matrix 320 may be used to determine the percentage of correct classification from all test points used through the iterations of the K-fold CV algorithm 318.

Referring now to FIG. 3B, the trained classifier 316 is used in the testing phase to determine a level of fouling from a heat exchanger 102. Sensor data 336 (also referred to as "testing sensor measurements"), such as the temperature, pressure, angular speed data from the sensors of FIG. 2 are obtained from the heat exchanger 102 and sent to an in-situ feature extraction process 330. The in-situ feature extraction process 330 includes a wavelet analysis process 332 and a data reduction process 334. The wavelet analysis process 322 and data reduction process 334 perform substantially the same processes as performed by the feature extraction process 302 of FIG. 3A. The outcome of these processes are the representative features (i.e., principal components) which are sent to the trained classifier 316, which makes a class decision based on the sensor data 336 to indicate a fouling class of the heat exchanger 102. The class decision may include a determination of a level of fouling or a recommendation to schedule maintenance for the heat exchanger/ECS or sending a notification to a pilot, in various embodiments.

The present invention therefore provides for early detection of heat exchanger fouling and identification of its severity level. The fouling diagnosis may be performed in the presence of various uncertainties in the system to minimize false alarms and missed detections. Maintenance of the aircraft heat exchanger may thus be performed based on the condition of the heat exchanger rather than using periodic maintenance procedures. Condition-based maintenance results in an increase of in-service usage of aircraft heat exchangers and hence additional aircraft usage.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A method of estimating a fouling state of a heat exchanger of an aircraft, comprising:
receiving, at a heat exchanger, at least one of bleed air or ram air from an aircraft engine;
coupling one or more sensors to the heat exchanger, wherein the one or more sensors include a pressure sensor configured to measure an input pressure of the bleed air to the heat exchanger, a temperature sensor configured to measure a temperature associated with the heat exchanger, and an angular speed sensor configured to measure a speed of a shaft of an air cycle machine of the aircraft;
obtaining training sensor measurements of a parameter related to operation of the heat exchanger;
applying a wavelet transform to the training sensor measurements to obtain wavelet data;
performing data reduction on the wavelet data to obtain a representative feature indicative of the training sensor measurements;
training a classifier to assign a suitable fouling class to the representative feature;
applying the trained classifier to testing sensor measurements from the heat exchanger to assign a fouling class to the testing sensor measurements in order to estimate the fouling state of the heat exchanger; and
evaluating a performance of the classifier to reduce a number of false alarms and missed detections by training the classifier, wherein the evaluation includes:
partitioning the training sensor measurements into a plurality of groups;
using a first portion of the plurality of groups to train the classifier and using a second portion of the plurality of groups to test the classifier;
generating a confusion matrix, the confusion matrix based at least in part on the testing of the classifier and which includes information associated with the performance of the classifier;
outputting the evaluation to a display;
determining at least one of a maintenance schedule or in-flight action based at least in part on the evaluation; and
performing maintenance of the heat exchanger based at least in part on a condition of the heat exchanger.

2. The method of claim 1, wherein the heat exchanger is included in an environmental control system having an air cycle machine, and the parameter further comprises at least one of: (i) heat exchanger output temperature; (ii) condenser inlet temperature; (iii) Environmental Control System output temperature; (iv) Environmental Control System input pressure; and (v) an angular speed of an Air Cycle Machine.

3. The method of claim 1, wherein the fouling class of the heat exchanger is known a priori.

4. The method of claim 3, further comprising classifying the representative feature using a pattern classification algorithm.

5. The method of claim 4, wherein training the classifier further comprises applying a cross-validation algorithm to test the ability of the classifier to correctly classify the representative feature.

6. The method of claim 1, further comprising obtaining the training sensor measurements from a model of the heat exchanger under different fouling conditions.

7. The method of claim 6, wherein training the classifier further comprises establishing fouling classification categories.

8. A method of estimating a fouling state of a heat exchanger of an aircraft, comprising:
receiving, at a heat exchanger, at least one of bleed air or ram air from an aircraft engine;
coupling one or more sensors to the heat exchanger, wherein the one or more sensors include a pressure sensor configured to measure an input pressure of the bleed air to the heat exchanger, a temperature sensor configured to measure a temperature associated with the heat exchanger, and an angular speed sensor configured to measure a speed of a shaft of an air cycle machine of the aircraft;

obtaining training sensor measurements of a parameter related to operation of the heat exchanger;

applying a wavelet transform to the training sensor measurements to obtain wavelet data;

performing data reduction on the wavelet data to obtain a representative feature indicative of the training sensor measurements;

training a classifier to assign a suitable fouling class to the representative feature;

applying the trained classifier to testing sensor measurements from the heat exchanger to assign a fouling class to the testing sensor measurements in order to estimate the fouling state of the heat exchanger;

evaluating a performance of the classifier to reduce a number of false alarms and missed detections;

outputting the evaluation to a display;

determining at least one of a maintenance schedule or in-flight action based at least in part on the evaluation; and performing maintenance of the heat exchanger based at least in part on a condition of the heat exchanger.

9. An apparatus for estimating a fouling state of a heat exchanger of an aircraft, comprising:
   a heat exchanger that is configured to receive at least one of bleed air or ram air from an aircraft engine, wherein the heat exchanger is coupled to one or more sensors;
   a model of the heat exchanger;
   one or more sensors configured to obtain training sensor measurements of a parameter related to an operation of the model of the heat exchanger, wherein the one or more sensors include a pressure sensor configured to measure an input pressure of the bleed air to the heat exchanger, a temperature sensor configured to measure a temperature associated with the heat exchanger, and an angular speed sensor configured to measure a speed of a shaft of an air cycle machine of the aircraft; and
   a processor configured to:
      apply a wavelet transform to the training sensor measurements to obtain wavelet data;
      perform data reduction on the wavelet data to obtain a representative feature,
      train a classifier to assign a suitable fouling class to the representative feature,
      apply the trained classifier to testing sensor measurements from the heat exchanger to assign a fouling class to the testing sensor measurements in order to estimate the fouling state of the heat exchanger;
      evaluate a performance of the classifier to reduce a number of false alarms and missed detections by training the classifier, wherein the evaluation includes:
         partition the training sensor measurements into a plurality of groups;
         use a first portion of the plurality of groups to train the classifier and using a second portion of the plurality of groups to test the classifier;
         generate a confusion matrix, the confusion matrix based at least in part on the testing of the classifier and which includes information associated with the performance of the classifier;
      output the evaluation to a display;
      determine at least one of a maintenance schedule or in-flight action based at least in part on the evaluation; and
      performing maintenance of the heat exchanger based at least in part on a condition of the heat exchanger.

10. The apparatus of claim 9, wherein the heat exchanger is included in an Environmental Control System having an air cycle machine and the parameter further comprises at least one of: (i) heat exchanger output temperature; (ii) condenser inlet temperature; (iii) Environmental Control System output temperature; (iv) Environmental Control System input pressure; and (v) an angular speed of an air cycle machine.

11. The apparatus of claim 9, wherein the processor is further configured to estimate the fouling state by performing a pattern classification algorithm on the representative feature to classify the representative feature.

12. The apparatus of claim 9, wherein the fouling class of the heat exchanger is known a priori.

13. The method of claim 12, wherein training the classifier further comprises applying a cross-validation algorithm to test the ability of the classifier to correctly classify the representative feature.

14. The apparatus of claim 9, wherein the processor is further configured to train the classifier using the model of the heat exchanger under different fouling conditions.

15. The apparatus of claim 9, wherein training the classifier further comprises establishing fouling classification categories.

* * * * *